(12) United States Patent
Sidebotham et al.

(10) Patent No.: US 8,523,866 B2
(45) Date of Patent: Sep. 3, 2013

(54) MODULAR TAPERED HOLLOW REAMER FOR MEDICAL APPLICATIONS

(76) Inventors: Christopher G. Sidebotham, Mendham, NJ (US); Randall J. Lewis, Bethesda, MD (US)

( * ) Notice: Subject to any disclaimer, the term of this patent is extended or adjusted under 35 U.S.C. 154(b) by 1011 days.

(21) Appl. No.: 11/973,260

(22) Filed: Oct. 5, 2007

(65) Prior Publication Data

US 2008/0195104 A1    Aug. 14, 2008

Related U.S. Application Data

(63) Continuation-in-part of application No. 11/704,754, filed on Feb. 9, 2007.

(51) Int. Cl.
  *A61B 17/00* (2006.01)
(52) U.S. Cl.
  USPC ............................................................. 606/80
(58) Field of Classification Search
  USPC .................. 606/79–80, 82–85, 86 R, 87–89, 606/95, 99
  See application file for complete search history.

(56) References Cited

U.S. PATENT DOCUMENTS

| | | | | |
|---|---|---|---|---|
| 1,629,581 A | * | 5/1927 | Machlet | 175/135 |
| 4,071,030 A | | 1/1978 | Hedrick | 606/196 |
| 4,116,200 A | | 9/1978 | Braun et al. | 605/81 |
| 4,811,632 A | | 3/1989 | Salyer | 76/115 |
| 5,078,718 A | * | 1/1992 | Moll et al. | 606/86 R |
| 5,100,267 A | | 3/1992 | Salyer | 407/54 |
| 5,116,165 A | | 5/1992 | Salyer | 407/54 |
| 5,171,312 A | | 12/1992 | Salyer | 606/81 |
| 5,171,313 A | | 12/1992 | Salyer | 606/86 |
| 5,190,548 A | * | 3/1993 | Davis | 606/80 |
| 5,236,433 A | | 8/1993 | Salyer | 606/91 |
| 5,282,804 A | | 2/1994 | Salyer | 606/86 |

(Continued)

FOREIGN PATENT DOCUMENTS

| | | | |
|---|---|---|---|
| EP | 88401621.3 | * | 6/1988 |
| WO | WO/9007908 | | 7/1990 |

OTHER PUBLICATIONS

"Effect of Flexible Drive Diameter and Reamer Design on the Increase of Pressure in the Medullary Cavity During reaming", Mueller et al., PubMed (1993) http://www.ncbi.nlm.nih.gov/entrez/query.fcgi?db=pubmed&cmd=Retrieve&dopt=AbstractPlus&list_uids=8168875&query_h1=2&itool=pubmed_Brief.

(Continued)

*Primary Examiner* — Matthew Lawson
(74) *Attorney, Agent, or Firm* — Ernest D. Buff; Ernest D. Buff & Assoc. LLC; Harry Anagnast, Esq.

(57) ABSTRACT

A reamer for medical applications comprising a shaft portion, a disposable tapered hollow reamer sleeve and a modular pilot. The shaft portion has a proximal end for attachment to a drill, a central cone element with one or more slots and a distal threaded end. The reamer sleeve has attached one or more torque transmitting tabs at the larger end and a collet taper at the smaller end and slides over the shaft engaging tabs with the slots. The modular pilot has a threaded central aperture engaging shaft thread and a collet taper mating with the collet taper of the reamer sleeve substantially coinciding their centerlines. The disposable hollow cutter sleeve has a plurality of cutting elements and apertures that discharge bone and bone cement debris into the space between the reamer and the shaft. With this construction, the reamer transmits reliable reaming torque in an efficient manner.

14 Claims, 7 Drawing Sheets

(56) References Cited

U.S. PATENT DOCUMENTS

| | | | | |
|---|---|---|---|---|
| 5,299,893 | A | 4/1994 | Salyer | 407/54 |
| 5,376,092 | A | 12/1994 | Hein et al. | 606/81 |
| 5,501,686 | A | 3/1996 | Salyer | 696/79 |
| 5,549,613 | A | 8/1996 | Goble et al. | 606/80 |
| 5,556,399 | A | 9/1996 | Huebner | 606/80 |
| 5,690,634 | A | 11/1997 | Muller et al. | 606/80 |
| 5,709,688 | A | 1/1998 | Salyer | 606/81 |
| 5,755,719 | A | 5/1998 | Frieze | 606/81 |
| 5,817,096 | A | 10/1998 | Salyer | 606/81 |
| 5,908,423 | A * | 6/1999 | Kashuba et al. | 606/80 |
| 5,954,671 | A | 9/1999 | O'Neill | 600/567 |
| 5,976,144 | A | 11/1999 | Fishbein et al. | 606/80 |
| 5,980,170 | A | 11/1999 | Salyer | 408/239 R |
| 6,001,105 | A | 12/1999 | Salyer | 606/81 |
| 6,120,508 | A * | 9/2000 | Grunig et al. | 606/85 |
| 6,162,226 | A * | 12/2000 | DeCarlo et al. | 606/80 |
| 6,168,600 | B1 * | 1/2001 | Grace et al. | 606/81 |
| 6,193,722 | B1 | 2/2001 | Zech et al. | 606/79 |
| 6,245,074 | B1 * | 6/2001 | Allard et al. | 606/80 |
| 6,332,886 | B1 | 12/2001 | Green et al. | 606/80 |
| 6,409,732 | B1 | 6/2002 | Salyer | 606/91 |
| 6,428,543 | B1 | 8/2002 | Salyer | 606/81 |
| 6,451,023 | B1 | 9/2002 | Salazar et al. | 606/86 |
| 6,505,687 | B1 * | 1/2003 | Wichmann | 172/22 |
| 6,517,581 | B2 * | 2/2003 | Blamey | 623/22.12 |
| 6,578,635 | B1 | 6/2003 | Hailey | 166/277 |
| 6,589,285 | B2 * | 7/2003 | Penenberg | 623/23.26 |
| 6,730,094 | B2 | 5/2004 | Salyer et al. | 606/80 |
| 6,854,742 | B2 * | 2/2005 | Salyer et al. | 279/93 |
| 6,875,217 | B2 | 4/2005 | Wolford | 606/81 |
| 6,951,563 | B2 * | 10/2005 | Wolford | 606/81 |
| 7,074,224 | B2 | 7/2006 | Daniels et al. | 606/80 |
| 2003/0078587 | A1 * | 4/2003 | Lechot et al. | 606/81 |
| 2003/0181916 | A1 | 9/2003 | Wolfdord | 606/81 |
| 2003/0212401 | A1 | 11/2003 | Nordman | 606/80 |
| 2004/0267266 | A1 * | 12/2004 | Daniels et al. | 606/80 |
| 2004/0267267 | A1 * | 12/2004 | Daniels et al. | 606/80 |
| 2005/0113836 | A1 | 5/2005 | Lozier et al. | 606/80 |
| 2005/0203525 | A1 * | 9/2005 | White et al. | 606/80 |
| 2006/0004371 | A1 * | 1/2006 | Williams et al. | 606/80 |
| 2006/0095041 | A1 | 5/2006 | Fehlbaum et al. | 606/81 |
| 2006/0106393 | A1 | 5/2006 | Huebner et al. | 606/80 |
| 2006/0184174 | A1 * | 8/2006 | Harris et al. | 606/80 |
| 2006/0195110 | A1 | 8/2006 | White et al. | 606/81 |
| 2006/0235539 | A1 | 10/2006 | Blunn et al. | 623/22.12 |
| 2006/0264956 | A1 | 11/2006 | Orbay et al. | 606/80 |
| 2007/0162033 | A1 | 7/2007 | Daniels et al. | 606/80 |
| 2007/0233127 | A1 * | 10/2007 | Tuke et al. | 606/79 |
| 2007/0233131 | A1 * | 10/2007 | Song et al. | 606/79 |

OTHER PUBLICATIONS

"Single Use Sterile Power Equipment", Orthomedix.com, at http://www.orthomedex.com/index.html.

* cited by examiner

Prior Art

Family of Disposable Reamer Sleeves

Singe Reamer Shaft- Multiple Reamer Sleeves

US 8,523,866 B2

MODULAR TAPERED HOLLOW REAMER FOR MEDICAL APPLICATIONS

This is a Continuation-In-Part of application Serial No. U.S. Ser. No. 11/704,754, Filed Feb. 9, 2007 for "Hollow Reamer For Medical Applications", the disclosure of which is hereby incorporated in its entirety by reference thereto.

BACKGROUND OF THE INVENTION

1. Field of the Invention

The present invention relates to a modular easy-to-assemble tapered hollow reamer for medical applications; and more particularly, to a hollow tapered reamer having a disposable reamer assembly, which can be attached to a reusable shaft portion and includes a bone debris capturing cavity.

2. Description of the Prior Art

Reaming of the internal canal of bones is required in many surgical procedures of orthopedic surgery. These procedures include hip replacement, knee replacement and shoulder replacement. Reamers are also used in procedures that involve the internal fixation of fractures. Prior art reamers typically fall into two major classes: rigid and flexible shaft. Typically, reaming of the internal bone canal is achieved through utilization of a solid cylindrical or tapered reamer. Solid cylindrical or tapered reamers currently utilized are required to cut both cancellous bone (spongy bone) and cortical bone (hard bone). Cortical bone is generally denser and stronger, requiring an efficient cutter to machine the canal for a proper fit of the implant. Conventional reamers can cut cortical bone initially but can quickly dull after a single use, or at best a few uses. Once the reamer has dull cutting edges, it reduces the efficiency of bone cutting and in addition generates sufficient friction/heat to damage or kill the surrounding bone. These prior art solid cylindrical or tapered reamers are intended for multiple uses and therefore become less efficient after each surgery, resulting in poor cutting performance and bone necrosis. These dull blades also incorporate bone debris or bone cement debris into the living bone tissue, creating bone healing problems.

U.S. Pat. No. 4,116,200 to Braun et al. discloses a milling tool for surgical purposes. The surgical milling tool is a hand-operated milling machine for milling the heads or sockets of bone joints and has a spherical shape. The tool is formed of a hemispherical cup integrally formed with a cylindrical skirt and flange and is provided with a plurality of openings of semi-oval shape, each having a cutting edge arranged at the minor axis of the oval shape. The openings are situated such that, upon rotation of the cup, the cutting edges thereof overlap to provide a continuous cutting edge surface conforming generally to the shape of the cup. The hemispherical shape of the cup provides the ability to hollow out the arcuate shape of the bone joints. Bone and cartilage shavings are formed during the milling process and are collected in a border area inside of the hemispherical cup. The surgical milling tool is provided for multiple uses and therefore the tool will become less efficient after each surgery, resulting in poor cutting performance and bone necrosis. Moreover, the spherically shaped reaming tool is not tapered.

U.S. Pat. No. 5,190,548 to Davis discloses surgical reamer. This surgical bone reamer includes a rotatable, elongated shank having a proximal end, a distal end and a longitudinal axis. A reaming head mounted on the distal end. A plurality of equally spaced walls is radially disposed on the reaming head around the longitudinal axis. Tip edges for penetrating bone are defined on the radial walls to be disposed angularly with the longitudinal axis. Reaming edges joined to the tip edges extend longitudinally from the tip edges in the proximal direction parallel to and an equal radial distance from the longitudinal axis for reaming a cylindrical tunnel when the reaming head is rotated in bone. Tapered flutes disposed angularly between the tip edges and the radial walls permit bone to be evacuated through the reaming head when forming a tunnel in bone. The reaming head is provided with angular tips and edges for penetrating the bone and is thus not a single use disposable cutter. The debris created is not stored away from the cutting edge and thus previously cut material may be included in the bone.

U.S. Pat. No. 5,549,613 to Goble et al. discloses a modular surgical drill. This modular surgical drill is in the form of a rigid drill shaft and a drill bit, which are connected together by a tongue-and-groove arrangement attaching the rear end of the drill bit to the forward end of the drill shaft. Each of the shaft and drill bit are provided with through bores extending centrally through their entire length. These bores become aligned upon assembly of the drill bit and shaft. The modular drill is intended to be employed with a guidewire for drilling holes into bone. The assembled drill bit and shaft are placed on the guidewire and moved down such guidewire into contact with the bone, whereupon a tunnel may be formed into the bone by rotating and advancing the drill bit along the guidewire. The dimensions of the bore and guidewire are so selected as to prevent the drill bit and drill shaft from moving relative to one another once they are assembled and mounted on the guidewire. Debris created during drilling is not removed and collected away from the cutting location. The central bore is solid and as such does not receive cut bone debris. The cutter used is not disposable.

U.S. Pat. No. 5,556,399 to Huebner discloses a bone-harvesting drill apparatus and method for its use. A coring drill harvests bone from a donor area of the human body. The drill bit is formed with a cylindrical, hollow shaft and a half-conical tip or cutting head. The cutting head is provided with a sharpened edge, which meets at an apex with a non-sharpened edge, forming an obtuse angle of approximately 120 degrees. The sharpened edge is configured to cut into bone when the drill bit is rotated in a clockwise direction. With the apex directed against a section of bone, the cutting edge sheers off fragments of bone, which are then drawn upwardly through the hollow shank of the drill bit. As the drill bit is forced downwardly, continuous cutting action occurs and the morselized bone can then be removed from the shank and used to build-up bone in other areas to which it is transplanted. The drill bit fittingly mates on the distal end a fitting that renders the drill bit physically compatible with a conventional chuck. The bit includes a pair of diametrically opposed, oppositely inclined recesses that cooperate with a crossbar member within a bit-receiving bore of the fitting. When the aligned drill bit is pressed into the fitting, the crossbar member cams along the inclined recesses causing the bit to rotate relative to the fitting. The resulting frictional engagement between the recesses and the crossbar member, along with a detent assembly between the bit and the fitting, securely lock the bit onto the distal end of the fitting, yet render removal possible by the use of a removal tool. The bone harvesting tool provides a non-disposable cutter. Reuse of the cutter dulls the beveled lip edges. Moreover, the harvested bone collection central bore requires a thorough cleaning prior to each use, creating contamination possibilities.

U.S. Pat. No. 5,690,634 to Muller et al. discloses a medullary drill head. This drill head for intramedullary drilling has a front part, a middle part and a rear part and is shaped as a hollow body of revolution. The front and rear parts have spiral slots formed with cutting edges. The rear part has an attachment for coupling to a drilling shaft. The drill head is not disposable, and as a result, the drill head is continuously reused, resulting in dulling of the cutting edges. Moreover, the drill head includes three openings in the form of spirally shaped slots configured to have cutting edges similar to a grater; and has no place to collect bone debris.

U.S. Pat. No. 5,954,671 to O'Neill discloses a bone harvesting method and apparatus. This apparatus and method harvests bone using a manual, cylindrical, multi-directional coring device with a guided delivery system that can be inserted through a percutaneous or closed approach to extract precisely measured amounts of bone or bone marrow. A series of guide wires, obturators, dilators and cannulas are used as the exposure and delivery instrumentation for a cutting tool. The cutting tool has a tip with six cutting edges for cutting in all directions. This apparatus is a manual, cylindrical, multi-directional coring device with a guided delivery system to extract precisely measured amounts of bone or bone marrow. The cutter portion of the device is not disposable and is subject to wear and dull edges. This coring device does not suggest a tapered reamer.

U.S. Pat. No. 5,976,144 to Fishbein et al. discloses a hollow dome reamer with removable teeth. This surgical reamer has a hollow dome with apertures spaced apart arranged in arcs extending from an apex of the dome to the base portion of the dome, and removable teeth positioned in the apertures. Each cutting tooth has (i) a flange that is aligned flush with the external surface of the dome, (ii) a raised cutting edge extending above the flange and the external surface of the dome, and (iii) an interior passageway communicating between the outside and inside of the dome. A base plate may be removably secured on the base portion of the dome to provide closure for the central cavity of the dome. Although the teeth are removable, they are not disposable in nature; the teeth are removed for replacement or for re-sharpening and are used again. Removal of the small teeth may be cumbersome and difficult, and may even pose a danger during removal as the person removing the teeth may be cut by the sharp edges; replacement of the teeth into the apertures of the reamer will likely pose the same problems. The bone debris is not collected away from the cutting edges of the teeth. This hollow domed reamer is spherically shaped reamer; does not suggest a tapered reamer.

U.S. Pat. No. 5,980,170 to Salyer discloses a tool driver. This tool driver has a shaft with a longitudinal axis and opposite ends. A boss is secured at one of the shaft ends by which the tool driver is connected to a rotary tool. A tool collate is secured at the other of the shaft ends by which the tool driver may be driven by a surgical hand piece having a chuck in which the collate may be positioned. The boss has a distal end surface with a groove therein. Both the groove and the distal end surface extend transversely of the axis. A pin is positioned in the groove on the axis. A latch mechanism is provided to hold a mounting bar of a rotary tool in the groove on the pin, whereby the rotary tool is held exactly coaxially of the driver during use. The rotary tool, which is used with the driver has a bar containing the same dimensions as the groove in the boss of the tool driver. The bar thus fills and is complementary to the slot. The bar has a hole therein which is complementary to the pin. The pin extends coaxially of the shaft and the boss. The bar hole in which the pin of the tool driver is positioned is precisely coaxial of the axis of the tool about which the cutting edges are precisely positioned. The cutters are connected to the tip of the shaft and are spherical in nature for joint and patella reaming. In addition, the reamer cups are not disposable in nature. The bone fragments are not collected and kept away from the cutting edge. This spherically shaped reamer is not tapered.

U.S. Pat. No. 6,193,722 to Zech et al. discloses a hollow milling tool. The hollow milling tool produces substantially hollow cylindrical depressions in human or animal tissue. It also produces tissue pillars, which are removed at a harvest location, transported to a defect location and implanted. The hollow milling tool has teeth for the ablation of tissue which are arranged at the distal end of the milling tool at the end side. Furthermore, the milling tool has passages for transporting a cooling fluid to a cooling region of the milling tool lying near the distal end during the ablation of tissue. Teeth are constructed within the milling tool for accomplishing the depressions. These teeth will eventually need sharpening as the tool is used over time. No structure is contained within the '722 patent that discloses or suggests a tapered reamer.

U.S. Pat. No. 6,332,886 to Green et al. discloses a surgical reamer and method of using same. This device is used for expedited reaming of a medullary canal. The device includes a reamer head connected at the distal end of a rotatable drive shaft. The reamer head has a cutting head with five blades and flutes therebetween. Each blade has a front cutting portion. The blades can also include a side cutting portion. The method for removing material from the medullary canal of a bone includes the steps of reaming an area of the medullary canal to remove material; irrigating the material to be removed while reaming to reduce generation of heat and move removed material from the reaming area; and aspirating the removed material while reaming to create a negative intramedullary canal pressure to assist in the removal of the material. The blades and flutes at the reamer are reused and are subject to dulling. The bone chips are to be removed by the irrigating fluid, which means they are always present adjacent to the cutting portions and may be forced into the bone tissue. No disclosure in the '886 patent suggests a tapered reamer.

U.S. Pat. No. 6,451,023 to Salazar et al. discloses a guide bushing for coring reamer, storage package for reamer assembly, and method of use. This guide bushing for a coring reamer has a tapered member with its largest diameter at its first end so that the guide bushing frictionally engages an internal surface of the reamer with a line contact. The guide bushing has a passage sized to slidably receive a guide pin. In use, the bushing advances in the proximal direction within the coring reamer along a guide pin while the excavated bone enters the passageway through the reamer. A storage package specifically designed for the reamer assembly is employed to remove the excavated bone from within the reamer. The package has a closed distal end and an open proximal end closeable with a cap. With the coring reamer received in cantilevered fashion through a central opening of the cap of the tube, and with an adapter that couples the coring reamer to a handpiece installed, a wrench is placed over the adapter and turned while the user grips peripheral surfaces of the cap to prevent rotation of the coring reamer. A plunger is inserted through the opening and through the coring reamer from the proximal end. The plunger is pushed through the reamer until the bone core and bushing fall out of the distal end of the coring reamer. The guide bushing for a coring reamer is appointed with an open end surrounded by peripheral teeth. The teeth are arranged peripheral to the body of the tube of the reamer. The tube is hollow and therefore excavated bone accumulates therewithin. The reamer, bushing and packaging are disposed of after use. The '023 patent discloses a bone excavating tool that does not prepare bone canal for implantation of femoral implants. No structure is disclosed therein that suggests a tapered reamer.

U.S. Pat. No. 7,074,224 to Daniels et al. discloses a modular tapered reamer for bone preparation and associated method. This kit is for use in performing joint arthroplasty and includes a trial and a reamer. The reamer is said to be useful when preparing a cavity in the intramedullary canal of a long bone with the use of a driver, and to assist in performing a trial reduction. The reamer includes a first portion for placement at least partially in the cavity of the long bone and a second portion operably connected to the first portion. The reamer is removably connected to the driver to rotate the reamer. The trial is removably attachable to the reamer. This tapered reamer is not disposable and does not have provision for accumulating bone debris away from the cutting portion of the bone.

U.S. Patent Application Publication No. 2005/0113836 to Lozier et al. discloses an expandable reamer. This expandable reamer includes a cannulated shaft and a plurality of straight cutting blades having deformable points. The blades are hingably outwardly rotatable at the deformation points between a contracted position and an expanded position. In the contracted position, the blades are substantially parallel to the longitudinal axis of the cannulated shaft and, in the expanded position, the blades have at least a portion oriented radially outward from the longitudinal axis, thereby forming a larger diameter cutting surface in the expanded position and in the contracted position. The blades are formed from a portion of the cannulated shaft by, e.g. milling longitudinally extending slots through the wall of the cannulated shaft. The slots serve as flutes dividing the cutting edge and trailing edge of each adjacent blade. Each blade may also include more than one segment arranged along its length, the segments being coupled by deformation points. The expandable reamer may be used for cutting a cavity in a bone or other structure that is larger than the diameter of the entry point into the bone and greater than the diameter of the contracted reamer. The expandable reamer is not disposable. Since the expandable blades are deformably attached to the cannulated shaft, the cut bone debris is not collected away from the bone cutting region. As a result, fragments of cut bone debris may be pushed into the bone tissue by the deformable rotating blades.

U.S. Patent Application Publication No. 2006/0004371 to Williams et al. discloses an orthopedic reamer. This orthopedic reamer is for use in creating and sizing canals in a bone. The orthopedic reamer includes a non-polymeric cutting portion having at least one cutting surface thereon and a polymeric body portion covering at least a portion of the cutting portion. The at least one cutting surface is not covered by the polymeric body portion. The orthopedic reamer provides cutting components including a blade or saw like construction, rather than the plurality of teeth. Although the orthopedic reamer is appointed for disposability, the publication requires that the entire reamer, and not just the cutting portion, be disposed of. That is to say, the entire reamer, including the non-polymeric cutting portion and the polymeric body portion of the device are all disposed of; not just the cutter.

There remains a need in the art for a modular easy-to-assemble hollow tapered reamer for medical applications having a disposable hollow cutter assembly. Also needed in the art is a disposable hollow cutter assembly of the type described, which can be attached to a reusable shaft portion that provides means for reaming of the internal canal of bones. Further needed in the art is a cutter assembly having means for collecting bone debris and keeping the collected debris displaced from the cutting edges, so that after one use of the reamer a new hollow cutter assembly can be utilized and the old hollow cutter assembly can be discarded.

SUMMARY OF THE INVENTION

The present invention provides a modular easy-to-assemble hollow tapered reamer for medical applications having a disposable cutter assembly. The cutter assembly is attached to a reusable shaft portion of the reamer and has a space for bone debris collection, which prevents inclusion of bone and bone cement debris into the living bone tissue. The reusable shaft portion has an integral or user attachable conical section containing one or more slots that receive the disposable cutter and thereby transfer shaft torque to the cutter. The reusable shaft is threaded at the distal end to secure the tapered hollow disposable cutter. A threaded modular pilot is provided with a collet that mates with the tapered hollow disposable reamer, thereby producing substantial coincidence of alignment between the centerline of the reamer with that of the reusable shaft. Preferably, a fresh tapered hollow reamer is used with each new application. Alternatively, the tapered hollow reamer is used several times and, after it has become worn or dull, is discarded. The tapered hollow reamer includes a plurality of apertures and is hollow to allow space between the reamer and the reusable shaft for bone and bone cement debris collection. It is attached to a shaft using a modular pilot with a threaded connection. When the modular pilot is tightened at the threaded end of the reusable shaft, the tapered collet of the modular pilot bears against the taper provided in the tapered hollow reamer, thereby causing substantially coincident alignment between the centerline of the reamer and that of the reusable shaft. The reamer portion is prevented from free rotation by one or more slots in the shaft cone element and tabs in the tapered hollow reamer. Torque from the shaft is transferred to the reamer, providing bone cutting action. Thus when a drill or other hand machinery rotates the reusable shaft, the shaft torque is transferred to the reamer through the tabs while the reamer is held securely at the centerline of the rotating reusable shift preventing any wobbly motion. This disposable sharp hollow reamer therefore reduces heat generated during cutting by removing the bone debris from the outer surface of the reamer to the inside of the reamer, while the bone debris collected may be used later for bone grafting and other specific surgical procedures. A further advantage of the hollow design is that by allowing the removal of the bone debris from the outer surface of the reamer to the inside of the cutter, the reamer is less likely to raise the intramedulary pressure in the long bone being reamed, thereby lessening the chance of fat embolism during these procedures. Also fragments of bone chips or bone cement are not incorporated in the living bone tissue by the reamer cutting action.

Generally stated, the reamer for medical applications comprises: (a) a reamer reusable shaft having an elongated body with a proximal end, a conical central element and a distal end, said proximal end having a coupling portion appointed for attachment of said reamer to a drilling device, said distal end having a threaded portion; (b) said central portion of said reamer reusable shaft having a pre-assembled cone element or a modular user assembled cone element having two or more lateral slots; (c) a disposable tapered hollow reamer comprising: (1) a disposable hollow reamer sleeve portion having an outer surface, said disposable hollow reamer sleeve portion further comprising a plurality of cutting teeth and a plurality of apertures on said outer surface; and at least one torque transmitting tab integrally attached to said hollow cutter sleeve at a larger diameter end designed to engage with at least one slot of said shaft conical central element, thereby transferring torque from said reusable shaft to said hollow tapered reamer sleeve; (3) the smaller diameter end of the tapered hollow cutter sleeve having a collet taper; (d) a modular pilot with an external collet taper that engages said collet taper of said hollow tapered reamer sleeve and a female threaded aperture for engaging with the shaft distal end threads and centering said tapered hollow reamer sleeve during assembly.

The present invention of modular tapered reamer solves the problems associated with the prior art reamers. In accordance with the present invention, the modular tapered hollow reamer for medical applications has an easy-to-assemble disposable modular hollow tapered reamer sleeve, which can be attached to a reusable shaft that allows for a fresh cutter assembly to be used with each new application of the reamer. The modular tapered hollow reamer of the present invention transfers shaft torque reliably while at the same time maintains the centerline of the reamer preventing wobbliness thereof during cutting. Bone and bone cement fragments are collected and stored away from the bone cutting area thereby reducing the possibility of bone fragment incorporation into living bone tissue. The modular tapered hollow reamer gradually crates the bone cavity due to the taper provided, thereby reducing heat during its surgical usage. Owing to the presence of these features, the modular tapered hollow reamer of this invention is safer to use and operates more efficiently than prior art reamers.

BRIEF DESCRIPTION OF DRAWINGS

The invention will be more fully understood and further advantages will become apparent when reference is had to the following detailed description of the preferred embodiments and the accompanying drawings, in which.

DESCRIPTION OF THE PREFERRED EMBODIMENTS

Figure 1:
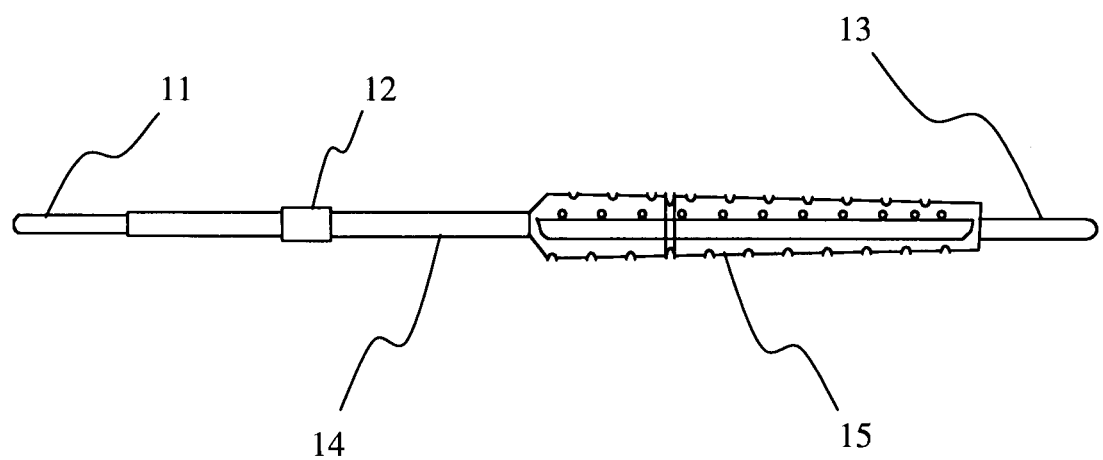
FIG. 1 is a perspective view depicting a medical tapered reamer found in the prior art.

Reaming of the internal canal of bones is required during many orthopedic surgical procedures. These procedures include hip replacement, knee replacement and shoulder replacement. Other surgical procedures that see the use of reamers include internal fixation procedures for fractures. Typically, reaming of the internal bone canal is achieved through utilization of a solid cylindrical or tapered reamer, illustrated in FIG. 1. Prior art reamers typically include a driver coupling 11 (shown as a Jacob chuck connector), a size designation 12, a pilot tip 13, a shaft 14, and cutting flutes 15.

FIG. 1 shows a tapered reamer, however cylindrical reamers of similar design also exist in the prior art. Those solid cylindrical or tapered reamers currently utilized are required to cut both cancellous bone (spongy bone) and cortical bone (hard bone). Cortical bone is generally denser and stronger, requiring an efficient cutter to machine the canal for a proper fit of the implant. Conventional reamers can cut cortical bone initially but can quickly dull after a single use, or at best a few uses. Once the reamer has dull cutting edges, it reduces the efficiency of bone cutting and in addition generates sufficient friction/heat to damage or kill the surrounding bone. The bone or bone cement debris collected is pushed against the living bone tissue and may be incorporated into the bone. Currently utilized solid cylindrical or tapered reamers are intended for multiple uses and therefore become less efficient after each surgery, resulting in poor cutting performance and bone necrosis.

Figure 2:
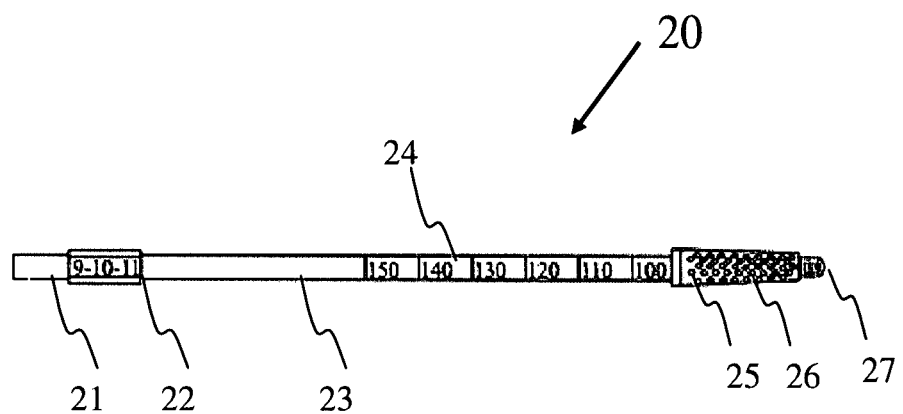
FIG. 2 is a perspective view depicting an easy-to-assemble modular hollow tapered reamer in accordance with the invention.

FIG. 2 depicts at 20 the modular disposable tapered hollow reamer assembly of the present invention, which provides the disposable hollow reamers appointed for use in medical applications. Due to its taper, it gradually enlarges the diameter of the bone canal reducing the amount of pressure applied to the bone. A number of sizes of tapered hollow reamers are available along with their shafts and modular pilots so that the surgeon can choose progressively larger hollow tapered reamers for a fresh bone canal or a reworked bone canal. Since the hollow reamer sleeves are disposable, the cutting performance of the hollow reamer is not compromised through repeated use. Several limitations of the prior art reamers and consequent clinical problems seen are overcome through utilization of the disposable modular tapered hollow reamers herein. Novel design features of the hollow reamers of the present invention and improvements to prior art reamers are multifaceted. The design includes a reusable shaft 23 with one or more lateral slots in a central conical section. A disposable tapered hollow reamer sleeve 26 is slid over the central conical section engaging torque transmitting tabs of the tapered hollow reamer sleeve with the slots. The disposable tapered hollow reamer is held in place by the modular pilot 27, which is screwed into the threaded distal end of the shaft 23. During this threaded attachment, a collet taper of disposable tapered hollow reamer sleeve 26 engages with a corresponding collet taper provided on the external surface of the modular pilot 27, substantially aligning the centerline of the disposable tapered hollow reamer sleeve 26 with that of the reusable shaft 23. The end of modular pilot 27 that is distal from the collet taper has a blunt or bullet shape, which facilitates centering of the tapered hollow reamer. The male thread of the shaft distal end and the female central thread of the modular pilot may be provided with a left-handed thread, so that the attachment does not come loose during the reaming operation. The shaft 23 is attached to a drill at 21. A number of shaft sizes can be selected from a kit and the shaft size is indicated at 22. The drill depth is indicated by depth markings 24. Shaft 23 has an integral or user attached cone section 25 and a disposable hollow reamer sleeve 26. The modular pilot may carry indicia representing a shaft size to which it may be connected. Preferably, the hollow reamer sleeve 26 is discarded after a single use to ensure a sharp cutter during surgery. Alternatively, the hollow reamer sleeve 26 is used several times and after becoming worn is discarded. Various techniques may be used to determine if the hollow reamer sleeve is worn enough to require disposal. Such techniques may include measurements of the sharpness of the hollow reamer sleeve. Moreover, when dealing with revision hip surgery, the hollow reamers have also been designed to cut bone cement (PMMA) in a more efficient manner by providing internal space 34 to capture the debris. This feature reduces both the cutting temperature and time required to remove the remnant cement mantle. The bone debris collected and removed may be used for bone grafting or other specific surgical procedures. A further advantage of the hollow design is that by allowing the removal of the bone debris from the outer surface of the reamer to the inside of the reamer, the reamer is less likely to raise the intramedulary pressure in the long bone being reamed, thereby lessening the chance of fat embolism during these procedures.

Figure 3:
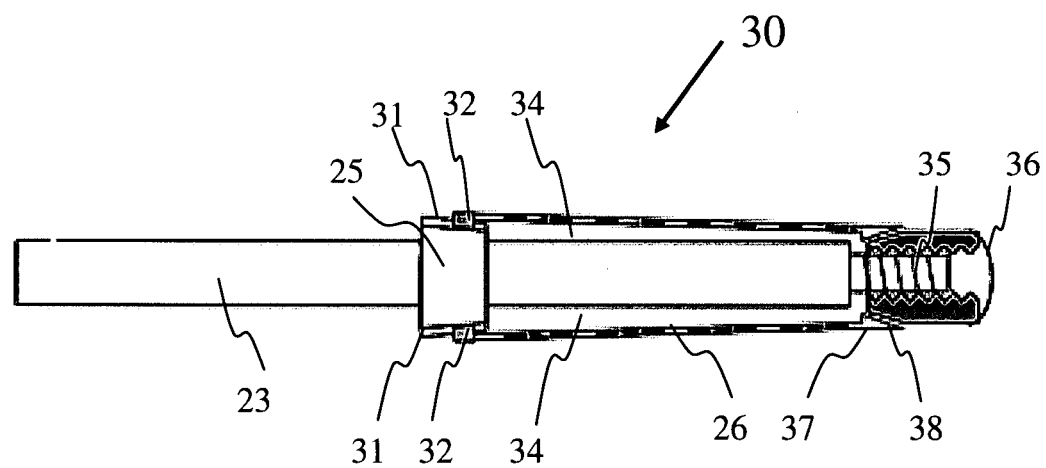
FIG. 3 is a cross sectional view of the easy-to-assemble modular hollow tapered reamer showing mechanical details in accordance with the invention.

FIG. 3 depicts at 30 the mechanical attachment details of the modular disposable tapered hollow reamer assembly. Identical indicia are used to keep track of various components. The reusable shaft 23 has the shaft cone element 25 with one or more slots 31, one above and one below are shown. The tapered hollow reamer sleeve 26 has two torque transmitting tabs 32 engaging into the slots 31 of the shaft cone element 25. As a result, when the shaft 23 is rotated, the tapered hollow reamer sleeve is also rotated with no slippage. The distal end of the tapered hollow reamer is provided with a collet taper as shown at 37. The distal end of the shaft 23 is threaded as shown at 35. A modular pilot 27 has female threads 36 that mate with the shaft distal end threads. The modular pilot has a collet taper at 38 that mates with the collet taper 37 of the tapered hollow reamer, centering the reamer as it is tightened. The space 34 that is between tapered hollow reamer sleeve 26 and the reusable shaft 23 receives the bone and bone cement debris.

Figure 4:
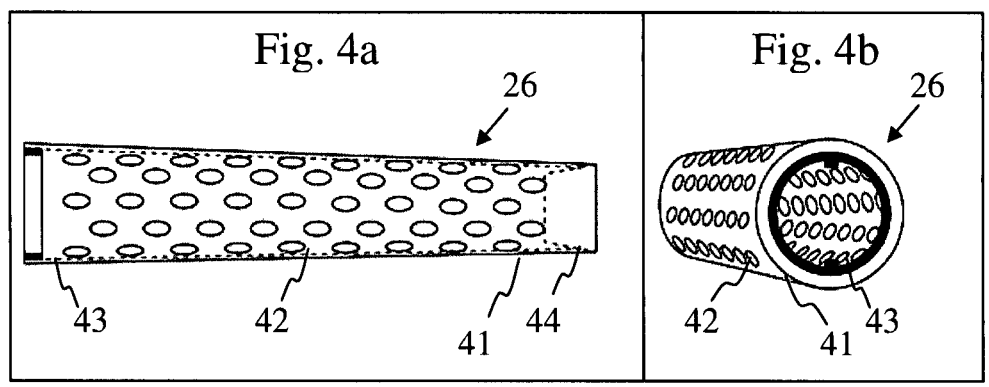
FIG. 4 depicts two views, FIG. 4*a* and FIG. 4*b* of the disposable hollow tapered reamer sleeve'

FIG. 4 illustrates in two views the design of the tapered hollow reamer sleeve. FIG. 4A is a front view depicting the disposable hollow reamer which has one or more torque transmitting tabs (two shown in the drawing) on the larger diameter end and a collet taper in the smaller diameter end. FIG. 4b shows a perspective view of the larger diameter end with two torque transmitting tabs. FIGS. 4A and 4B depict at 26 the disposable hollow reamer sleeve, which comprises: (i) a disposable hollow reamer sleeve portion having an outer surface 41 having a hollow construction, the disposable hollow reamer sleeve portion further comprising a plurality of cutting teeth 42 and a plurality of apertures (also at 42) on the outer surface 41; (ii) a plurality (two shown) of torque transmitting tabs 43 integrally attached to the tapered hollow reamer; at the larger diameter end and (iii) a collet taper 44 on the smaller diameter end. Preferably, the cutting teeth 42 protrude from the outer surface of the disposable hollow cutter sleeve, consequently forming the plurality of apertures. Alternatively, the plurality of apertures can be separate and distinct from the cutting teeth on the outer surface of the disposable hollow cutter sleeve.

The thickness of the hollow reamer sleeve portion should impart sufficient strength to withstand offset loads and axial loads on the reamer shaft during advancement of the cutter. The amount of load that can be tolerated without warping or changing the accuracy of the machined cavity can be determined by laboratory tests, which replicate clinical usage of the instrument. Typically, the disposable hollow reamer sleeve portion has a wall thickness ranging from 0.005 to 0.039 inch. Preferably the wall thickness of the hollow reamer sleeve portion ranges from 0.010 to 0.032 inch, and most preferably from 0.012 to 0.015 inch. These thickness facilitate cutting by a disposable, low cost, hollow reamer sleeve in an accurate, efficient and reliable manner.

Figure 5:
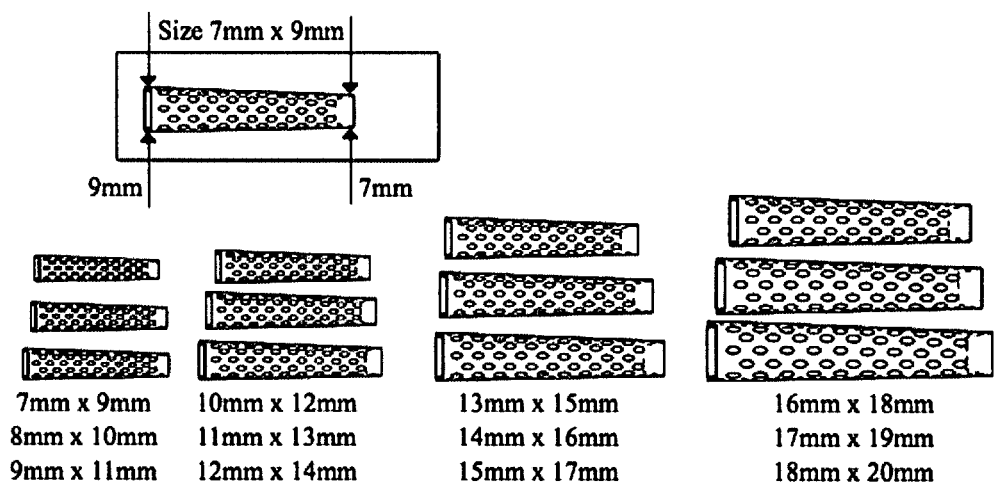
FIG. 5 illustrates a family of disposable tapered hollow sleeves incorporating the elements of the present invention.

FIG. 5 illustrates a family of disposable tapered hollow sleeves provided. The family of disposable tapered hollow sleeves provided according to the present invention addresses a wide range of bone sizes, including sizes ranging from 7 mm through 20 mm in one (1) mm increments; and being tapered and having a 7 mm tapering to a larger diameter in one (1) to three (3) mm increments and having size options from a 7 mm base dimension to a 20 mm base dimension in one (1) mm increments.

Figure 6:
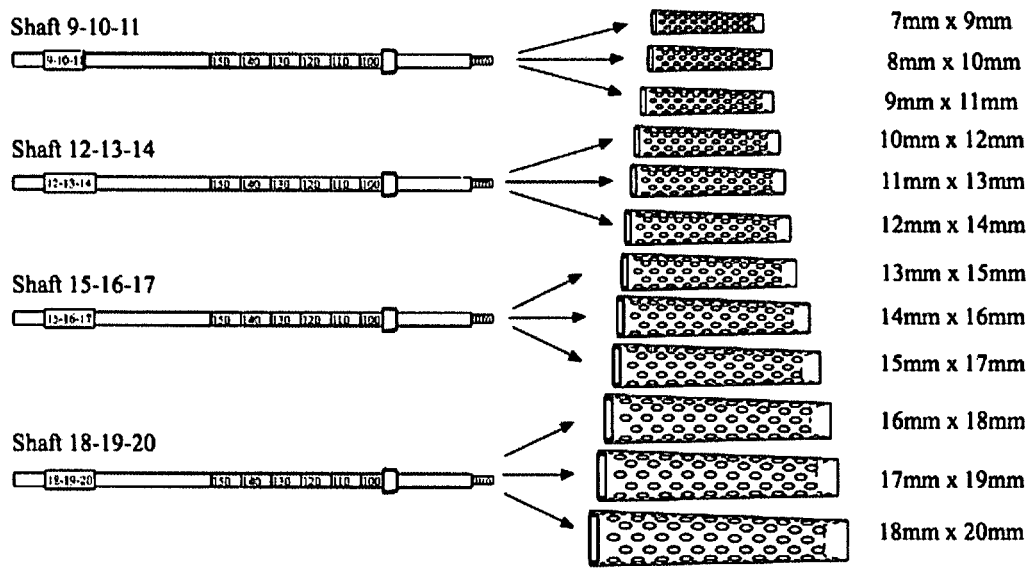
FIG. 6 depicts multiple disposable tapered hollow sleeves attached to a single shaft.

Multiple disposable tapered hollow sleeves can be attached to a single shaft, as is illustrated in FIG. 6. Preferably, a single shaft will attach to at least three different sized disposable hollow cutter assemblies. This provides for the ability to combine various sized shafts with various sized disposable hollow cutter assemblies. These reusable reamer shafts have a coupling on the proximal end and a threaded portion in the distal end. The shaft portion between the proximal end and the central portion may be made flexible to facilitate insertion of the tapered hollow reamer. Each reusable shaft has an integrally attached or user attachable modular cone element with one or more lateral slots for receiving the torque transmitting tabs of the tapered hollow reamer sleeve, as shown in FIG. 4B, and a threaded portion at the distal end for retaining the modular pilot in accordance with the invention.

Figure 7:
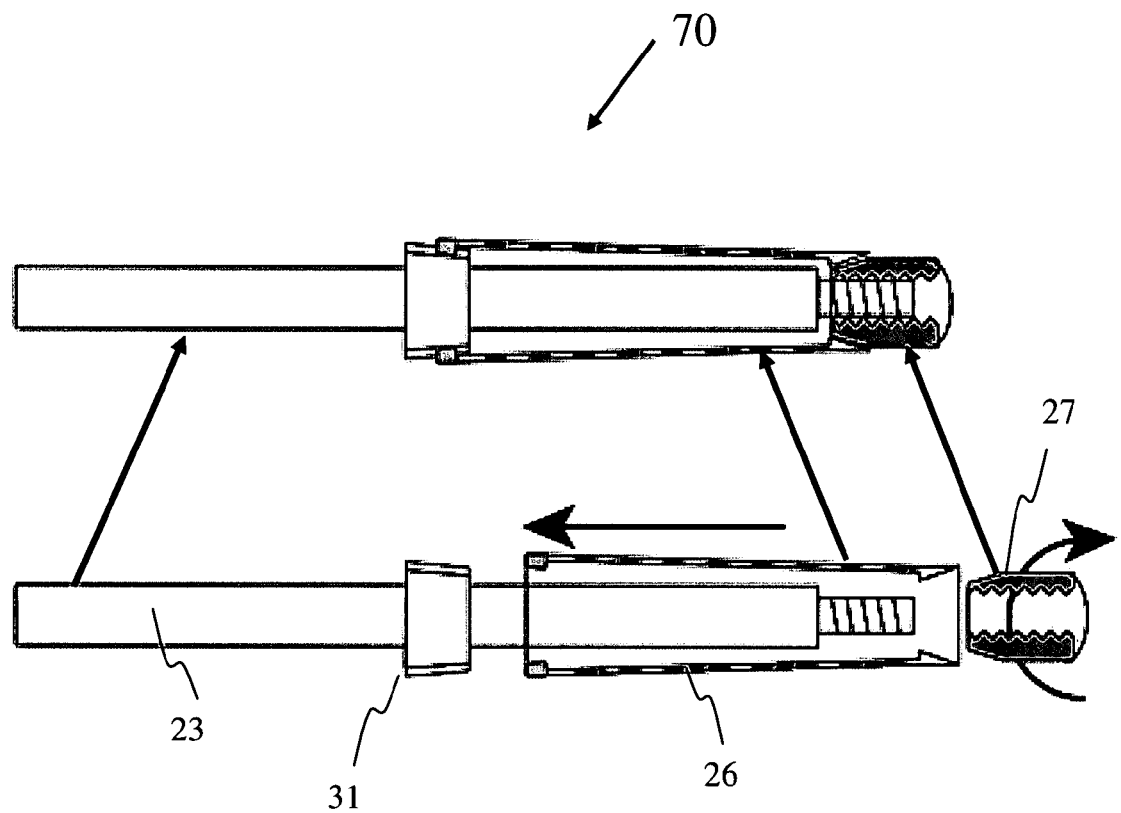
FIG. 7 provides an assembly view depicting the tapered hollow reamer assembly.

FIG. 7 provides an assembly view depicting the tapered hollow reamer assembly. The assembled taped hollow reamer and the three component parts are shown. The hollow reamer sleeve 26 is inserted over the cone section 31 of the reusable shaft 23 with the torque transmitting tabs of the tapered hollow reamer sleeve 26 positioned within the shaft cone section lateral slots. The modular pilot 27 is screwed on to the end of the reusable shaft, capturing the disposable tapered hollow reamer sleeve. The collet taper is provided at the end portion of the tapered hollow reamer sleeve, and the modular pilot substantially aligns the centerline of the tapered hollow reamer sleeve with the centerline of the reusable shaft.

Figure 8:
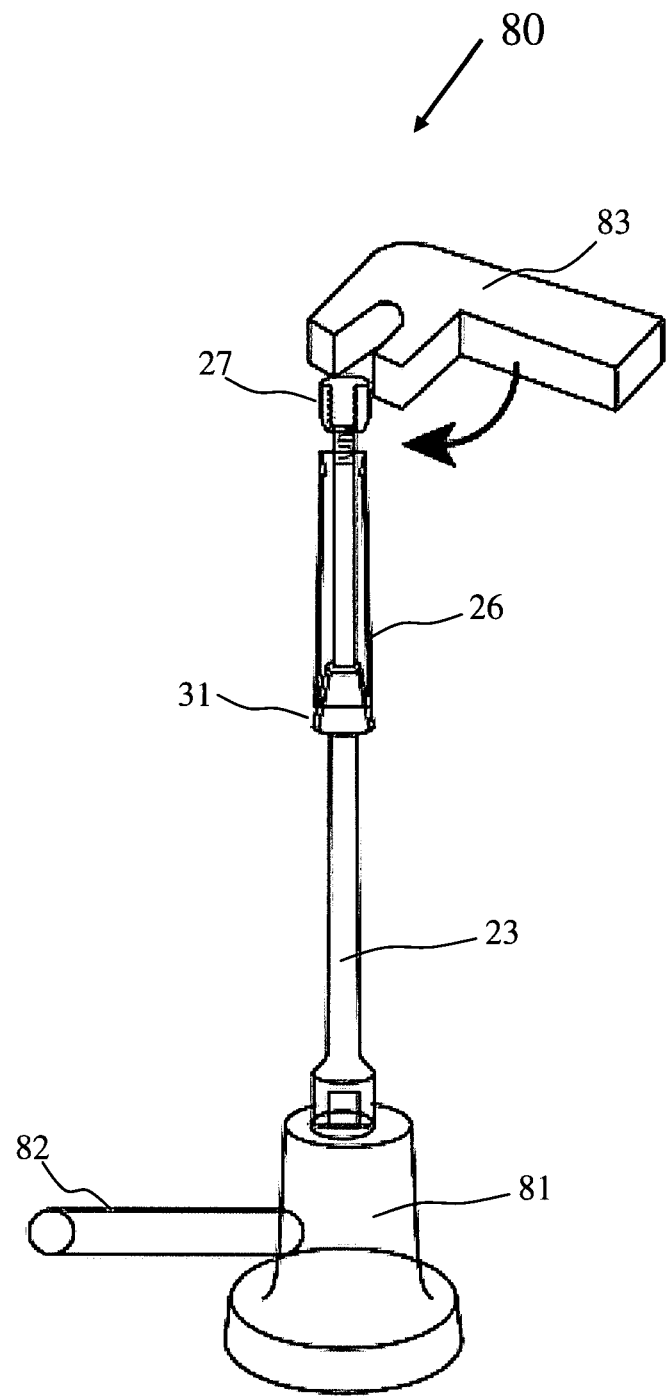
FIG. 8 depicts an alternate embodiment of the tapered hollow reamer assembly.

FIG. 8 depicts an alternate embodiment of the tapered hollow reamer assembly. Since the reusable shaft 23 has a coupling suited for attachment to a drill at the proximal end, it may be placed in a vice or chuck 81 to secure the reusable shaft in a vertical position, as shown. Next the tapered hollow reamer sleeve 26 is inserted over the shaft as shown, engaging the torque transmitting tabs of the tapered hollow reamer sleeve with the lateral slots provided at the cone section 31 of the reusable shaft 23. Next, the modular pilot is screwed into the threads at the distal end of the reusable shaft 23 and is tightened with a wrench 83. The modular pilot may be provided with a set of notches to accommodate a wrench. A handle 82 attached to the vice or chuck 81 provides support during this tightening procedure.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. A reamer for medical applications to be used for reaming a bone canal, comprising:
   a. a shaft portion having an elongated body, comprising:
      i. a proximal end having a coupling portion appointed for attachment of said reamer to a drilling device;
      ii. a central conical element having one or more lateral slots; and
      iii. a distal end having a male threaded portion;
   b. a disposable tapered hollow reamer sleeve having a substantially conical shape, comprising:
      i. an outer surface and a hollow interior said outer surface having a plurality of cutting teeth and a plurality of apertures;
      ii. a larger diameter end with at least one integrally attached torque transmitting tab; and
      iii. a smaller diameter end with a collet taper;

c. a modular pilot with a central aperture having female threading and an external surface with a collet taper, an end of said modular pilot that is distal to said collet taper of the modular pilot has a bullet shape;

d. said disposable tapered hollow reamer sleeve being adapted to slide over said distal end of said shaft portion, whereby said one or more slots of said central conical element engage with said at least one torque transmitting tab of said tapered hollow reamer sleeve; and e. said modular pilot being appointed for insertion said distal end of said shaft portion, whereby:
  i. said male threaded portion of said distal end of said shaft portion engaging engages with said female threading on said central aperture of said modular pilot and;
  ii. said collet taper on the external surface of said modular pilot engages with said collet taper of said hollow reamer sleeve;

whereby said disposable tapered hollow reamer sleeve is appointed to ream the bone canal; and whereby torque from the shaft portion is transferred to said tapered hollow reamer sleeve with substantial coincidence of centerlines, preventing reamer wobbliness, and bone and bone cement debris is collected in a space between the tapered hollow reamer sleeve and shaft portion.

2. A reamer for medical applications as recited by claim 1, wherein said shaft portion is reusable.

3. A reamer for medical applications as recited by claim 1, wherein said threaded portion of said distal end of said shaft portion has a left-hand male thread for assembly into said modular pilot having the female threading that is left handed.

4. A reamer for medical applications as recited by claim 1, wherein said elongated body of said shaft portion further comprises a plurality of graduations to determine the depth of said disposable tapered hollow reamer sleeve in a canal of a bone during use.

5. A reamer for medical applications as recited by claim 1, wherein said elongated body of said shaft portion further comprises a marking to indicate its size.

6. A reamer for medical applications as recited by claim 1, wherein said modular pilot further comprises a marking to indicate its size.

7. A reamer for medical applications as recited by claim 1, wherein said modular pilot includes a flat portion being appointed for insertion with a wrench.

8. A reamer for medical applications as recited by claim 1, wherein said disposable tapered hollow reamer sleeve is appointed for a single, one-time use.

9. A reamer for medical applications as recited by claim 1, wherein said disposable tapered hollow reamer sleeve is appointed for more than a single use depending on the amount of damage to said disposable tapered hollow reamer sleeve after its initial use.

10. A reamer for medical applications as recited by claim 1, wherein said shaft portion is solid.

11. A reamer for medical applications as recited by claim 1, wherein said shaft portion is rigid.

12. A reamer for medical applications as recited by claim 1, wherein said tapered hollow reamer sleeve has a wall thickness ranging from 0.005 to 0.039 inch.

13. A reamer for medical applications as recited by claim 12, wherein said sleeve has a wall thickness ranging from 0.010 to 0.032 inch.

14. A reamer for medical applications as recited by claim 13, wherein said sleeve has a wall thickness ranging from 0.012 to 0.015 inch.

\* \* \* \* \*